(12) United States Patent
Beikoff (10) Patent No.: US 9,504,615 B2
(45) Date of Patent: Nov. 29, 2016

(54) MULTIPURPOSE FIRST AID APPARATUS

(71) Applicant: Tracey Maree Beikoff, Mareeba (AU)

(72) Inventor: Tracey Maree Beikoff, Mareeba (AU)

( * ) Notice: Subject to any disclaimer, the term of this patent is extended or adjusted under 35 U.S.C. 154(b) by 0 days.

(21) Appl. No.: 14/426,288

(22) PCT Filed: Sep. 5, 2013

(86) PCT No.: PCT/AU2013/001009
§ 371 (c)(1),
(2) Date: Mar. 5, 2015

(87) PCT Pub. No.: WO2014/036604
PCT Pub. Date: Mar. 13, 2014

(65) Prior Publication Data
US 2015/0224001 A1    Aug. 13, 2015

(30) Foreign Application Priority Data
Sep. 5, 2012 (AU) .................... 2012903853

(51) Int. Cl.
| A61F 17/00 | (2006.01) |
| A61F 5/37 | (2006.01) |
| A61F 7/00 | (2006.01) |
| A45F 4/00 | (2006.01) |

(52) U.S. Cl.
CPC ............. *A61F 17/00* (2013.01); *A61F 5/3738* (2013.01); *A61F 7/0085* (2013.01); *A45F 2004/003* (2013.01)

(58) Field of Classification Search
CPC .... A61F 17/00; A61F 5/3738; A61F 7/0085; A61F 2007/0001; A61F 7/02; A45F 2004/003; A45F 3/04
USPC ........................................................ 224/577
See application file for complete search history.

(56) References Cited

U.S. PATENT DOCUMENTS

| 3,889,684 | A | * | 6/1975 | Lebold | A61F 7/02 607/109 |
| 4,580,555 | A | * | 4/1986 | Coppess | A61F 5/0585 602/23 |
| 4,880,315 | A | * | 11/1989 | Berry | A45C 13/02 150/113 |
| 5,101,815 | A | * | 4/1992 | Langdon-Orr | A61F 5/05841 128/876 |
| 5,862,916 | A | * | 1/1999 | Utecht | A41D 19/0055 206/278 |
| 5,967,390 | A | * | 10/1999 | Goryl | A01K 97/05 224/153 |
| 6,230,952 | B1 | * | 5/2001 | Jupiter | A45F 3/04 150/113 |
| 2003/0000987 | A1 | * | 1/2003 | Barr | A45C 7/009 224/661 |
| 2004/0121672 | A1 | * | 6/2004 | McLarty | B63B 22/12 441/113 |
| 2006/0288466 | A1 | * | 12/2006 | Bucheit | A41D 13/0012 2/102 |
| 2008/0035523 | A1 | * | 2/2008 | Lemire | A45C 13/005 206/774 |

(Continued)

*Primary Examiner* — Corey Skurdal
(74) *Attorney, Agent, or Firm* — Tredecim LLC; Sean L. Sweeney (57) ABSTRACT

The invention relates to a multipurpose first aid apparatus for a person or animal including, a body adapted for carrying items, securing means for use with the body; and at least one attachment means. In use, at least one attachment means can be used to attach the body so as to be transported with the person or animal. The items can be carried within or about the body and in the case of an injury to a limb of the person or animal, the body can be used with the securing means, to firmly support the limb of the person or the animal until professional medical or veterinary assistance can be sought. The invention also relates to variants of the apparatus and a method of use.

13 Claims, 7 Drawing Sheets

(56) References Cited

U.S. PATENT DOCUMENTS

| | | | |
|---|---|---|---|
| 2009/0127045 A1* | 5/2009 | Williams | A45C 7/0059 190/107 |
| 2009/0163095 A1* | 6/2009 | Weinel | A62B 33/00 441/114 |
| 2012/0152986 A1* | 6/2012 | Van Art | A45F 3/20 224/148.2 |
| 2013/0110027 A1* | 5/2013 | Kobler | A61F 13/0273 602/75 |
| 2015/0041511 A1* | 2/2015 | Powell | A45C 13/18 224/576 |

* cited by examiner

MULTIPURPOSE FIRST AID APPARATUS

FIELD OF THE INVENTION

The present invention relates to a multipurpose first aid apparatus, and in particular to a multipurpose first aid apparatus for use to carry first aid apparatus and be itself used as first aid apparatus in the case of an emergency.

BACKGROUND OF THE INVENTION

In the specification the invention is described with reference to the example of use by a horse rider and horse, as this is one of many useful applications of the invention. However, the invention can be used for a great many different situations, including with other animals and for other activities. It is not intended that the invention be in anyway limited to use by a horse rider and horse.

Many people live, work or visit "outback" Australia or other similar harsh environments. For example, mine works may be visiting a remote potential site for testing or investigation, or farmers may be working the land. Recreationally people enjoy walking, camping, fishing, biking, and other outdoor pursuits in the outback, and also closer to urban conurbations. People may walk with a dog or other pet, or go horse riding, on the land. Each and all of these activities can be dangerous, at times, and in particular if you are out of phone range or some distance from immediate medical or veterinary assistance. In such circumstances a temporary fix is required to splint or support an injury so that the person or animal can be stabilised to be moved to obtain medical care at a hospital, for example.

In a remote outback or bush environment breaking a leg or arm can be a very serious thing and medical assistance must be sought and obtained as soon as possible. Similarly, if a horse is injured on a ride, it is desirable to be able to stabilise any injury and improve the comfort of the horse to facilitate getting to help.

A person may injure themselves away from home but can only contact the emergency services or call for medical or veterinary assistance by returning home. With less serious injuries such as cuts and scratches, it is also preferable to be able to treat these as soon as possible to make the injured person as comfortable as possible and to protect the injured area for the journey home.

A first aid kit containing useful items may be carried by a person, when away from home, containing useful items for medical treatment in case of injury or accident. These known kits are generally of a standard hard box form and cannot be readily carried by a person, or rider of a horse or quad bike, for example. Further, carrying of a hard box could contribute to an accident on impact, and so is undesirable for outdoor use. A soft form first aid kit for use by horse riders may be attached to the horse's strapping but will strike or rub on the horse as riding, making it most uncomfortable. First aid supplies can be put into saddle bags but these are not convenient to carry all the very many items as are required for first aid in an emergency. Saddle bags can cause sweating and friction as they sit directly on the horse's skin and bounce or chafe with the riding movement. The only alternative is for the rider to wear a backpack or bum bag to carry first aid supplies which is extremely uncomfortable during the movement of riding. Further, the rider carrying a bag causes problems with balance, as well as distracting the rider if making adjustments Large items of medical or veterinary apparatus such as splints and supports are not convenient to carry when working or riding outdoors but would be incredibly useful in the event of an accident. For example, in the situation where a person has sprained or broken a wrist having a temporary support or splint would dramatically improve the comfort and assist them to get to help or to wait until help arrived. In remote areas there is no mobile phone coverage and unless the person has a satellite phone or radio, help cannot be called until the person gets back to base. In these situations any medical assistance that can be applied in the field will reduce the pain of the person and improve their ability to get to help and not be stranded.

Similarly, if out riding a horse, the animal may injure its leg on a ride, leading to blood loss; suitable bandages, antiseptic and electrolyte replacement should be carried and applied to assist the horse to get to where veterinary assistance can be organised. Where the injury is more serious, such as a break or fracture, treatment will need to wait until the rider can get the horse to assistance.

It would be most desirable to be able to have a multipurpose first aid apparatus that can be conveniently and comfortably carried by a person in the case of an accident. Further it would be most desirable to have a multipurpose first aid apparatus that can be used to support an injured limb. Further it would be useful to have a multipurpose first aid apparatus that can be used for both a person and an animal in the case of injury.

For clarity, any prior art referred to herein, does not constitute an admission that the prior art forms part of the common general knowledge, in Australia or elsewhere.

It is an object of the present invention to provide a multipurpose first aid apparatus that at least ameliorates one or more of the aforementioned problems of the prior art.

DISCLOSURE OF THE INVENTION

Accordingly, the present invention provides a multipurpose first aid apparatus for a person or animal including:
 a body adapted for carrying items;
 securing means for use with the body; and
 at least one attachment means,
wherein, in use, at least one attachment means can be used to attach the body so as to be transported with the person or animal, and the items can be carried within or about the body and in the case of an injury to a limb of the person or animal, the body can be used with the securing means, to firmly support the limb of the person or the animal until professional medical or veterinary assistance can be sought.

The invention is applicable to many situations where it is desirable to carry first aid items, and or to support an injury, and has numerous useful and beneficial applications. The attachment means may be omitted from the invention, such as where used carried behind the seat of a vehicle.

The person may be any suitable person. The person may be someone who travels or works in remote areas. The person may be a person who enjoys outdoor pursuits. The apparatus may be used for a person chosen from the group: mountaineers; hiker; casual walker; rider, including horse rider, motorbike rider, cyclist and quad bike rider; dog walker; pastoralist; and people working in the transport, utility or mining industries. The invention may be used for workers in the field, such as workers for utility companies, including electricity. These workers may use the invention in their vehicles or outside in the field in case of accident or emergency. There is a key advantage to the subject invention over the prior art in that the body protects the contents and will not crack or rattle during transportation when made of a soft material, and can also be readily be taken into the field.

The animal may be any suitable animal. The animal may be any animal that a person wishes to ride or walk with outdoors. The invention can be used for any animal, such as domestic animals including a dog and cat, or beasts of burden, including a horse, donkey, mule, or camel. The apparatus may be used for a horse rider and horse.

In one form of the invention the apparatus is able to be used for both the person and an animal. The apparatus may be adapted for use to support the injured limb of either a person or animal. In other words the same apparatus can be used to treat an injury of the person or animal, whichever becomes injured. The apparatus may be available in a range of formats. The range of formats may be chosen from the following: equine/human; canine/human; bike/human; and human "Outback" version. Any suitable combination of animal and human transportation may be used. Preferably, the body is adapted for use to support the injured limb of a person and a particular animal. Preferably, in this form of the invention the items may also be suitable for treatment of the person and the particular animal. In other forms of the invention the apparatus is adapted for use by a person only, such as in a remote "outback" environment. In other forms of the invention the apparatus is adapted for use by a person only, such as in a remote "outback" environment or other dangerous or isolated place. The invention may also be used closer to cities such as for hiking in national parks or other green spaces, or in any suitable environment whether remote or urban.

Preferably, the body is a substantially planar body. Preferably, the body can be rolled up during transportation. Preferably, the body is a substantially planar body to enable it to be rolled up during transportation. The rolling up may be in a similar manner to a swag. Preferably, the body is a substantially planar body to enable it to be rolled up during transportation and be unrolled and wrapped or rolled around the limb of the person or animal to support the limb in case of injury.

Preferably, the substantially planar body is made of a strong material suitable for outdoor use. Preferably, the substantially planar body is made of canvas. The canvas may be heavy duty "12 oz canvas". Preferably, the body is substantially waterproof, water resistant or splash proof. Preferably, the substantially planar body is substantially waterproof, water resistant or splash proof as may be suitable to the particular application. Preferably, the substantially planar body includes a waterproof cover. Any suitable material or combination of materials may be used for the substantially planar body.

Preferably, the substantially planar body is rolled up before transportation. In one form of the invention the substantially planar body may be rolled up before attachment to the rider or a saddle. Preferably, the substantially planar body is unrolled before use to support an injured limb. Preferably, the substantially planar body is folded in half before being rolled up for use. Items may be carried in the folded or rolled up body. The substantially planar body preferably includes at least one closure to close the body in the folded state. Preferably, the closure is one or more zip. Preferably, a zip is included to surround the body in the unrolled, folded state and after unzipping the body can be unfolded. Preferably, the body can be closed in a substantially waterproof manner. In another form of the invention hook and loop fasteners may be used instead.

The substantially planar body may be any suitable size as is convenient to carry for the particular application. Preferably, the body is made of soft material. In this form of the invention the soft material does not suffer from the problems of the prior art of impacting other hard surfaces during transportation, making unnecessary noise and causing damage to itself, other items or potentially the person in the case of an accident. Preferably, the substantially planar body is made of a soft material so that in the case of an impact the apparatus does not cause injury to the person or animal. Where the person is a rider of an animal the apparatus may be carried so as not to impact or contact rider or animal during a ride. Where the person is riding a vehicle such as a motor-bike, the apparatus may be configured particular to not impact or contact the person during transportation. Preferably, the apparatus protects the person or animal from impact if they land on the apparatus. Preferably, the soft nature of the apparatus means it is convenient and comfortable to use by the rider and horse when horse riding.

Preferably, the adaptation to carry items can be a plurality of different forms or ways. For example, the body may include pockets, compartments, or sections to suit different types or sizes of items, including internal and external pockets. Preferably, at least one external pocket is included. Preferably, an external pocket is included that enables ready access to items during transportation.

Preferably, items can be carried in the substantially planar body in the rolled or folded state. Preferably, at least one pocket is included, configured to lie inside the body when the body is in the rolled state. Preferably, items can be placed in the or each pocket and protected from the elements. Preferably, the or each pocket is substantially waterproof. Preferably, the or each pocket is made of transparent material to allow items to be easily found and retrieved from the or each pocket. Preferably, the or each pocket includes a closure. The closure may be any suitable closure. Preferably, the closure is a zip lock to keep the items within the pocket and prevent ingress of water or dust. Preferably, the or each pocket is removable from the body. The or each pocket may be attached to the body by any suitable means. The or each pocket may be attached by a zip, hook and loop fasteners, or press studs, for example. Alternatively, the pockets may be made integrally with the body.

Preferably, items carried for use by the person may be chosen from the group: alcohol swabs; amputated parts bag; antiseptic cream; antiseptic swabs; bandages; bandage-conforming elastic gauze; burn gel; burn dressing; burns and scalds information sheet; butterfly closures; compression bandage; combined dressings; crepe bandage; disposable resuscitation mask; dressing combined pad; eye pad; eye wash bath; eyewash saline ampoules; first aid pamphlet; gloves; hand sanitizer; heavy bandages; incident report notebook & pen; insect repellent; instant ice pack; lip balm; low adherent dressings; major accidents item sheet; minor accidents item sheet; non-adherent dressings; pain killers; paper tape; pencil and notebook; plasters; iodine swabs; press seal bags; safety pins; scissors; snake bite information sheet; splinter probes; sunscreen; thermal blanket; torch; triangular bandages; tweezers; and wound dressings. Internal and external pockets may be included to carry items.

Where the apparatus is used for a quad bike rider or similar items may be carried chosen from the group: carbon dioxide cartridges and insulator; reamer tool; vehicle instruction manual; hook tool; tyre plugs; cutting knife; rubber solution; and inflator tube.

Where the apparatus is used for a person and a horse one pocket may be included, for keeping items for use in case of sickness or injury to the horse. Items that may be kept in the or each pocket for treatment of a sick or injured horse be chosen from the group: hoof pick; pliers; bandages, syringe, electrolyte paste or powder; and sterile gauze swabs. Any suitable items for use for a horse could be carried within one or more pocket. Where the apparatus is used for a person and animal the items included may be chosen from the group: pliers; bandages, syringe, electrolyte paste or powder; sterile gauze swabs; and items specific to the type of animal, for example a hoof pick for a horse.

Multiuse items may be carried in one or more pocket. The multiuse items may include: first aid instruction sheets; a survival book; scissors; forceps; tweezers; antiseptic; gloves; sodium chloride pods; saline ampules; thermal blanket; bandages; and gauze or cotton wool. Most preferably, three internal pockets are included and one pocket substantially contains items for use for the animal and another pocket substantially contains items for use by the person. All the pockets may be used to carry items for use by the person instead.

Preferably, at least one outer pocket is included on the outer surface of the substantially planar body. Preferably, an outer pocket is included adapted to be at the top outer surface of the substantially planar body so that in use the pocket can be readily accessed during transportation. The outer pocket may be removable. Preferably, the outer pocket is adapted to contain and protect a mobile phone or similar device. Preferably, the outer pocket includes padding. Preferably, the outer pocket includes a strong closure to keep the mobile phone safe during a ride or in the case of an accident. Preferably, the outer pocket protects a mobile phone or other contents but also allows ready access by the person during transportation. Where the apparatus is used by a rider of an animal or vehicle the outer pocket may be configured to enable access, such as to a mobile phone, while riding. The particular position, size shape and number of pockets can be varied to suit the particular application and desires of a particular user.

Preferably, a personal locating beacon is included. Preferably, the personal locating beacon may be included and carried in an outer pocket of the apparatus for ready access at any time.

Preferably, the at least one securing means includes at least one strap. Preferably, the at least one securing means includes hook and loop fastenings. Most preferably, the securing means includes hook and loop fastenings and a pair of straps. The securing means may include different fastenings to use the apparatus to support different limbs. For example, the body may be rolled tightly around a leg and secured with a pair of straps to stabilise a broken leg. Alternatively, the body may be formed into a tube and secured with a fastening such as a hook and loop fastening to support an injured arm. Most preferably, straps are included which can be attached to body so that the body can be supported about the neck of the person to support an injured arm. Alternatively, one or more strap can be used to tightly wrap the body around an arm. The method of use of the apparatus will vary, depending on the nature of the injury. It is one of the many benefits of the invention that it can be adapted for use of not only people and animals but for a range of different injuries to different limbs.

Any suitable number of straps may be used. Preferably, at least a pair of straps is used. Preferably, a pair of straps are included each attached to the outer surface of the substantially planar body. Preferably, each of the pair of straps is attached close to one end of the strap close to a top region of the substantially planar body so that the body can be rolled up and the straps attached to the body wrapped around the body and secured to maintain the body in the rolled up state. Preferably, the body is wrapped and secured by the straps in a similar manner to a swag. Preferably, each strap includes a fastener. The fastener may include a receiving part and a projecting part which reciprocate to fasten firmly together in use. Any suitable fastener may be used. Alternatively, the straps may be tied around the body to maintain the body in the rolled state. The at least one strap used to wrap the body around a limb to be supported may be omitted, in an alternative form of the invention, and be replaced by another securing means. Any suitable securing means may be used to firmly and securely wrap the body around a limb to be supported.

One or more extra strap may be included. The or each extra strap may be attached to the outer surface of the body. Preferably, the or each extra strap includes a fastener to firmly close the strap. Preferably, at least one extra strap is included not attached to the substantially planar body. Preferably, an extra strap is included that can be used as a support for a sling by attaching to either end of the body at the attachment means and sling around the neck of the person, the arm of the person that is injured being wrapped in the body. Preferably, at least one extra strap is carried in one of the internal pockets.

Preferably, use of the straps with the substantially planar body includes as a sling, strut, or any suitable support of an injured part of the person or animal to support a joint or to slow bleeding. Preferably, the substantially planar body is unrolled and then wrapped tightly around the part of the person or animal to be supported. The body may be wrapped around a leg of the horse to support a fracture, for example. The body may be wrapped tightly around the leg of the person where a fracture, break or other injury has occurred. The body may be wrapped around the arm of a person to act as a sling or support in case of an injury to the hand, arm or shoulder where support is beneficial. Preferably, hook and loop fasteners are included at suitable positions on the body such that the body can be folded or rolled and secured through use of the hook and loop fastener to form a sling into which the arm of the person can be put.

The support may be to stabilise an injured limb including a broken bone. The support may be to compress a limb. The compression may be used to slow bleeding. The support may be a combination of stabilising a broken bone and compression to slow bleeding or swelling. Preferably, the body also acts to protect an injury from dirt and further damage.

Preferably, once the body is wrapped around an area it is desired to support the or each strap is used to maintain the body in place. The two straps may be attached to the body and in use in an emergency situation both of these straps are wound around the body and the area of the body of the person or animal and secured tightly. The tight winding may aid to stabilise the limb and or provide compression to reduce swelling and stop bleeding. Extra straps may be included to further secure the body. The extra strap may be used to support the body such as a sling where the person wraps their injured arm in the substantially planar body in the unrolled (but not unfolded) state and tightly wraps two straps around before attaching a third strap about the neck of the person and to either end of the body, thereby relieving the person of the weight of the injured arm. More preferably, hook and loop fasteners are included at suitable positions on the body such that the body can be folded or rolled and secured through use of the hook and loop fastener to form a sling into which the arm of the person can be put. Preferably, a strap attached to the body can be put about the neck of the person and reattached to the body of the apparatus to support the injured arm in the sling.

Attachment means are included for securely attaching the apparatus for transportation. The attachment means may take any suitable form. The attachment means may attach the apparatus to the person, animal or to an object. The attachment means may be attachment by means of a belt loop through which a belt of a person can be threaded to securely and conveniently transport the apparatus. The attachment means may include fasteners chosen from the group: strap; clip; hook and loop fastening; tie; clasp; or a combination thereof. The attachment means may attach to something attached to a person, animal or object. For example, an item of clothing, saddlery or similar. The attachment means may be adapted to attach the apparatus to a vehicle or other means of transport. The vehicle may be chosen from the group: motor bike; quad bike; car; ute; truck; or boat. The attachment means may be attached to a post or pole. The attachment means may be attached to the rear of a motor bike, quad bike or bicycle. Preferably, the attachment enables at least some of the items can be readily accessed during transportation. The attachment may be to any part of a vehicle.

Where the person is a horse rider on a horse the apparatus may be attached to a saddle. Preferably, the apparatus is attached to the saddle so that it does not contact the horse when being ridden. Preferably, the apparatus is attached behind the rider to the saddle so as not to contact or inconvenience horse or rider.

Transportation may be riding on a horse or other beast of burden. Transportation may be by being taken by a vehicle from one location to another location. Transportation may be riding on a bicycle, motor bike, quad bike or the like. Transportation may be by any suitable means.

Preferably, one or more reflective strip is included on the outer surface of the body. Preferably, a reflective strip is included towards the top of the outer surface of the substantially planar body so that in use in the rolled up state the reflective strip runs across the back of the apparatus improving visibility of the person during low light or poor visibility.

Preferably, at least part of the apparatus can be used to contain water. The water may be contained in the apparatus in the unfolded state. The water may be contained in one or more pocket. A waterproof pocket or liner for a pocket may be included specifically for containment of water. The waterproof pocket or liner may be removable or be made integral with the body. Preferably, the waterproof pocket or liner may be made of any suitable material. The waterproof pocket may be made of PVC. The water may be cold water, warm water or contain ice as is appropriate to the injury to be treated. The apparatus may have water put into it and sealed using a water proof closure for transportation of the water. The apparatus may be wrapped around a limb to provide support with the water creating a compression of the wound. Any suitable means to contain the water may be used.

Preferably, in one form of the invention water can be put in a waterproof and sealable part of the body before application to an injured limb to aid compression. In this case the water may be at ambient temperature, or if available iced water. Use of the water, including chilled or iced water can facilitate compression of the injury reducing swelling and bleeding until medical or veterinary assistance can be sought or obtained.

Accordingly the invention also provides a method of use of a multipurpose first aid apparatus for a person or animal including a substantially planar body, one securing means for use with the body and one or more attachment means, the method including the following steps:
a) putting items inside one or more pocket formed in the substantially planar body;
b) rolling up the substantially planar body and securing with one or more securing means; and
c) attaching the rolled up body and straps with the attachment means for transportation with the person or animal, wherein, in the event of an injury to the person or animal the rolled up body and securing means can be readily detached by use of the attachment means and unrolled to enable items to be retrieved for treatment of the person or animal.

Preferably, the method includes the further steps of:
d) wrapping the substantially planar body around an injured limb and securing tightly with the securing means so that the limb is supported.

The method may also include use of water in one or more part of the substantially planar body. The water may be transported this way, used to wash an injury or provide hydration to a horse, for example. Water may be used in the body to increase the compression properties when applied to an injured limb.

The method may also include removal of one or more pockets containing first aid items before use as a support for an injured limb.

The multipurpose first aid apparatus of the method may be the multipurpose first aid apparatus according to the invention in any of its forms or variants.

INDUSTRIAL APPLICABILITY

The multipurpose first aid apparatus is manufactured industrially in parts before being assembled and supplied to retailers in kit form for on-sale, or for direct marketing.

BRIEF DESCRIPTION OF THE DRAWINGS

The invention will now be described in connection with a non-limiting preferred embodiment with reference to the accompanying drawings, in which.

DETAILED DESCRIPTION OF THE INVENTION INCLUDING A BEST MODE

Referring to FIGS. 1 to 9, a preferred embodiment of the invention will be described, used for a horse rider and horse as a useful example of the invention. Other forms of the invention may be used for a person only, or for a person and any other animal, such as a dog. The person may also use the invention when riding a motor bike, quad bike or bicycle, for example. Although described here for a horse and horse rider the same apparatus and method of use can be used in the other situations, although the contents of the apparatus may be varied to suit the particular application, as mentioned elsewhere.

As illustrated the multipurpose first aid apparatus 1, includes body 10 with straps 12 and 14, and anchors 16 and 18. Apparatus 1 is adapted to be made of strong durable materials suitable for use outdoors and to be tolerant to heat, sunlight and rain. Body 10 as illustrated is made of a strong canvas material known as "12 oz" weight, similar to that used for swags and resistant to ingress of water. Other strong and weatherproof materials may be used instead such as plastics or vinyl. Body 10 is made of a strong material but is soft, and so will not easily be damaged or contribute to or cause injury through impact.

Body 10 is illustrated as 670 millimeters by 500 millimeters and 30 millimeters thick when in the unrolled and unfolded state. When folded body 10 has dimensions of 335 millimeters by 500 millimeters by 30 millimeters thick. When rolled body 10 reduces to 120 millimeters wide by 335 millimeters and 110 millimeters thick. The dimensions used are convenient to carry apparatus 1 during use and to apply body 10 to a limb, as described in more detail below.

Figure 1:
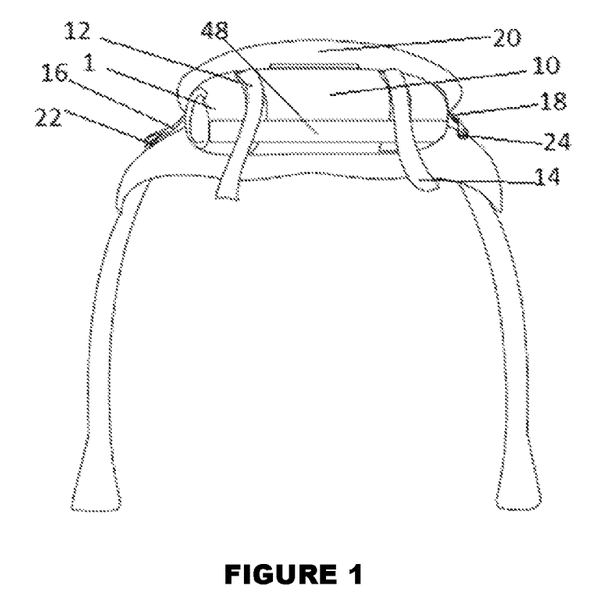
FIG. 1 is a perspective view from behind of a multipurpose first aid apparatus according to a preferred embodiment of the invention attached.
Figure 2:
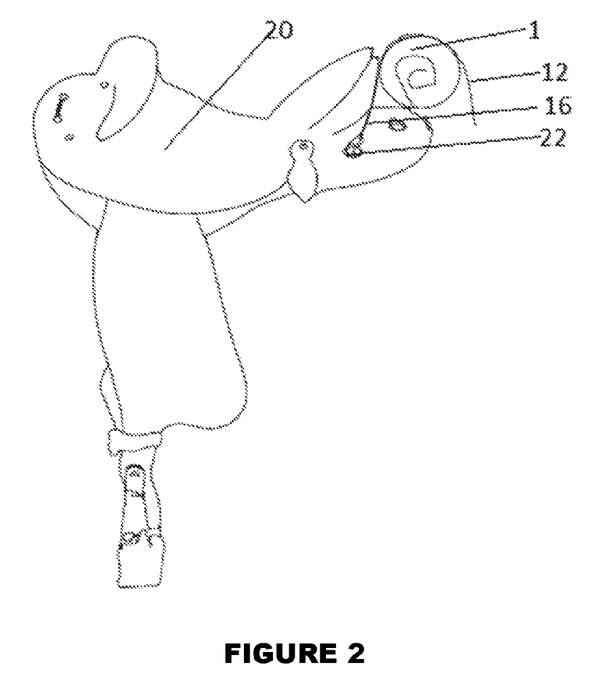
FIG. 2 is a side view of the multipurpose first aid apparatus and saddle of FIG. 1.

Referring to FIGS. 1 and 2 in particular saddle 20 is shown as would be used on a horse (not shown for ease of illustration). Saddle 20 includes loops 22 and 24 as is usual and it to these loops that anchors 16 and 18 respectively attach. Other forms of saddle include leather straps or saddle cloth as attachment points for apparatus 1 to the saddle instead of loops 22 and 24. Anchors 16 and 18 are illustrated as metal clips that can be pressed to open to enable passing over loop 22 or 24 and then released to close clipping the anchor to the loop in a strong manner. The anchor will not release from the loop until a person again presses to open the clip and moves the anchor out of the loop. Any suitable secure clip or fastening can be used instead of anchors 16 and 18. Anchors 16 and 18 are particular useful as they can be very easily released for access to apparatus 1 and similarly quickly reattached to the back of saddle 20. Where apparatus 1 is used attached to a person, this may be through use of a belt loop incorporated in body 10 through which the person can thread their belt to securely attach apparatus 1 to themselves. Clearly many different forms of attachment can be used depending on to what apparatus 1 is to be attached. Where apparatus 1 is to be attached to a vehicle such as a motor bike a clip or strap may be used. In other forms of the invention apparatus 1 may be placed or secured behind the seat of a vehicle.

The positioning of apparatus 1 for use with a horse has been carefully considered and devised to be a convenient location for use by the rider during a ride but most importantly does not inconvenience the horse. Apparatus 1, when attached through use of anchors 16 and 18 and loops 22 and 24, is in a raised position just behind the rider. The position means that apparatus 1 does not contact the back of the horse or bump on the horses back, causing discomfort. Since apparatus 1 is also not being carried by the rider there is no additional discomfort to the rider either, which is advantageous. Similarly, when carried by a rider of motor bike, quad bike or similar apparatus 1 can be similarly mounted behind the rider to enable easy access during a ride without inconveniencing the rider during use.

To remove apparatus 1 anchors 16 and 18 are unclipped and apparatus 1 is then free to be removed completely for use.

Figure 3:
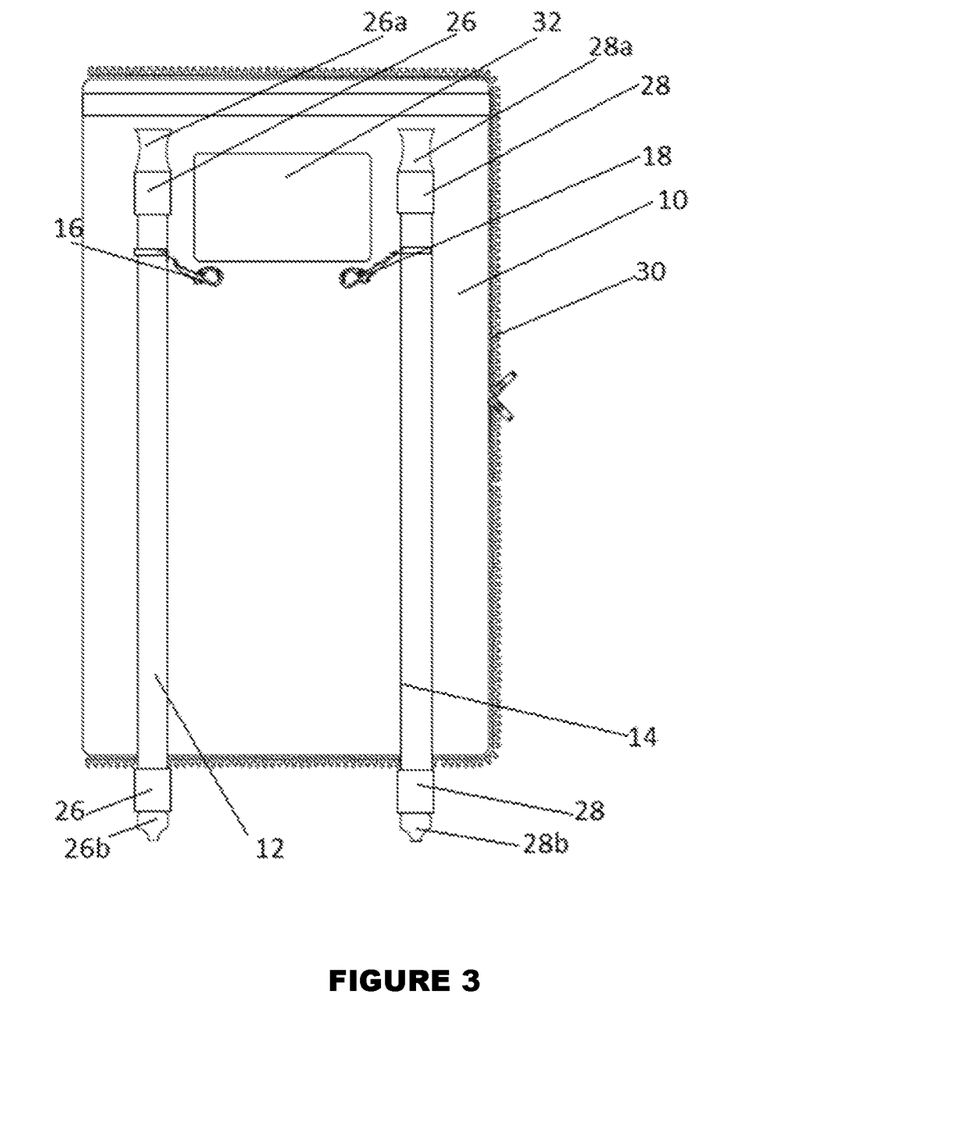
FIG. 3 is a plan view from above of the multipurpose first aid apparatus of FIGS. 1 and 2 in an unrolled state.

Referring to FIG. 3 in particular apparatus 1 has been removed and clips 26 and 28 of straps 12 and 14 respectively unclipped. Clips 26 and 28 as shown are plastic clips of a known kind having receiving parts 26a and 28a and projecting parts 26b and 28b. Therefore, strap 12 has receiving part 26a at one end and is attached to body 10 close to that end; the other end has projecting part 26b. Similarly, strap 14 has receiving part 28a at one end and is attached to body 10 close to that end; the other end has projecting part 28b. In use straps 12 and 14 hang loose from body 10 except where attached so that body 10 can be rolled up and once rolled up straps 12 and 14 can be wrapped around the rolled body 10 and then held in the rolled position by use of clips 26 and 28. The manner of rolling and securing the straps is similar to that used for a swag. To unroll body 10 the process is reversed so that clips 26 and 28 are unclipped releasing straps 12 and 14 so they can be unwound. Once unwound body 10 can be unzipped using zip 30 to be a similar length to straps 12 and 14. Zip 30 is a strong zip as used with canvas material and runs around the edge of body 10 on three sides.

Outer pocket 32 is made of strong "12 oz" canvas, including a padded interior and strong, reliable zip (not shown). Alternatively, plastic or vinyl could be used for pocket 32 and the padding omitted if desired. Pocket 32 is adapted to be positioned at the top of apparatus 1 when rolled up and attached to saddle 20. The positioning is important to enable use to keep a mobile phone or similar communication device when riding while keeping it convenient for use. The rider can simply reach behind him or her and access the mobile from the pocket at any time during a ride. Use of the canvas and strong zip is beneficial to prevent the mobile phone from getting splashed by water, or mud and most importantly to prevent ingress of dust. The padding also protects the mobile phone while travelling along. A personal locating beacon is also included in outer pocket 32 for ready access and activation in the case of an emergency. The contents of outer pocket 32 can be varied as is suitable to a particular application.

Figure 4:
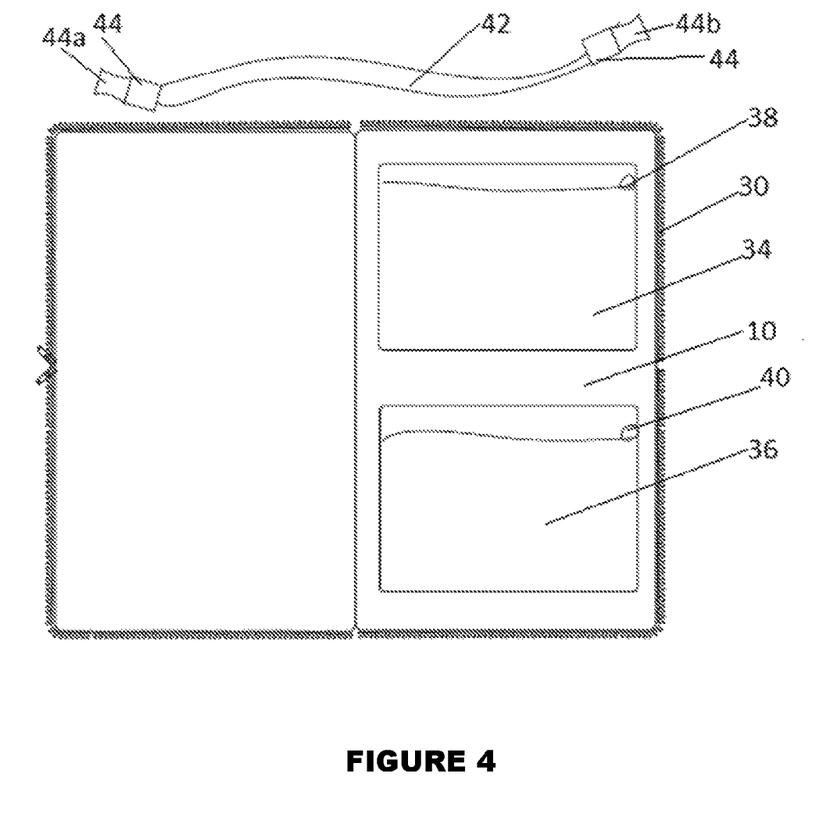
FIG. 4 is a plan view of the multipurpose first aid apparatus of FIGS. 1 to 3, showing the inside when rolled out and unzipped.

Referring to FIG. 4 in particular apparatus 1 has been detached, unrolled and unzipped and then unfolded to reveal inner pockets 34 and 36. Three or more inner pockets may be included instead. Inner pockets 34 and 36 are removed for use as a support for a limb by means of zips (not shown). Inner pockets 34 and 36 have the dual purpose of being used to contain items and for use in an emergency, as described further below. Any items may be carried within pockets 34 and 36. As illustrated it is intended for pocket 34 to be used as an equine survival pouch to contain useful items increase of illness or injury to the horse. These items may include a hoof pick, pliers, bandages, swabs, syringe, electrolyte powder and any other items that it may be desired to be carried. For other uses the items included can be varied to suit the needs of the person, animal or a vehicle for which the apparatus is to be used.

Pocket 36 is used as a human survival pouch for items useful for treatment of the rider in the case of a medical emergency. Items may include hand sanitiser, lip balm, insect repellent, plasters, paper tape, bandage conforming elastic gauze, non-adherent dressing, crepe bandage, triangular bandage, safety pins, eyewash saline ampoules, dressing combined pad, wound dressings, burn aid gel, press seal bags, antiseptic swabs, pencil and notebook, alcohol swabs, disposable resuscitation mask, torch, splinter probe, sunscreen, eye pad, antiseptic cream, pain killers, bandages including a compression bandage. Either pocket 34 or 36 may also include items for use for treatment of either the horse or rider, including first aid instruction sheets, forceps, saline ampoules, bandages, a survival book or other useful literature, scissors, tweezers, antiseptic, gloves, sodium chloride pods, thermal blanket, gauze or cotton wool. Any items that may be deemed useful in a particular environment can be carried in either pocket 34 or 36, or for use for a person or animal. Other arrangements of pockets could be used. However, the segregation of items into those for use for the horse and items for use by the rider is a convenient way to assist to find items quickly. Where apparatus 1 is used just for a person all the items will be useful for the person, and the different pockets can be used to segregate items as is useful for ease of retrieval of the items. Where the apparatus is used on a bike or quad bike for example, or other vehicle items useful for emergency situations for use of the bike, quad bike or other vehicle may be included in one pocket of the apparatus. Where the apparatus is used with for a person and a dog one of the pockets may contain items useful for treatment of the dog in the case of accident or injury.

Pockets 34 and 36 are illustrated as clear plastic pockets so that the contents can be seen clearly and any item required easily found and removed for use. It may be important to make finding items as easy as possible as in an emergency situation shock or panic may cloud the mind of the person making it difficult to do things such as to locate a compression bandage to stop bleeding. Each pocket 34 and 36 can be closed by zip lock closures 38 and 40 to prevent items from falling out. Zip lock closures 38 and 40 seal pockets 34 and 36 enabling them to be waterproof. The waterproofing stops water or dust from getting inside pockets 38 and 40 damaging the contents. A waterproof liner or insert can be carried in one of the pockets, taken out and put in the pocket for use as a water carrier.

Extra strap 42 is also carried in either pocket 34 or 36 for use when body 10 is being used to support an injury. Extra strap 42 includes clip 44, having receiving part 44a and projecting part 44b, the same as for straps 12 and 14.

Figure 5:
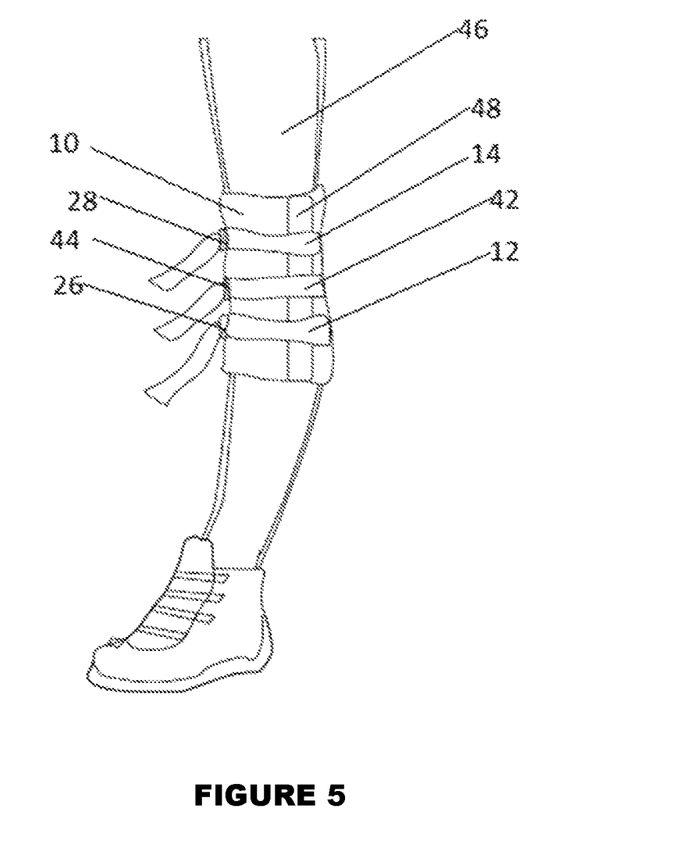
FIG. 5 is a perspective view from the side of the multipurpose first aid apparatus of FIGS. 1 to 4 in use to support the rider's injured leg.
Figure 6:
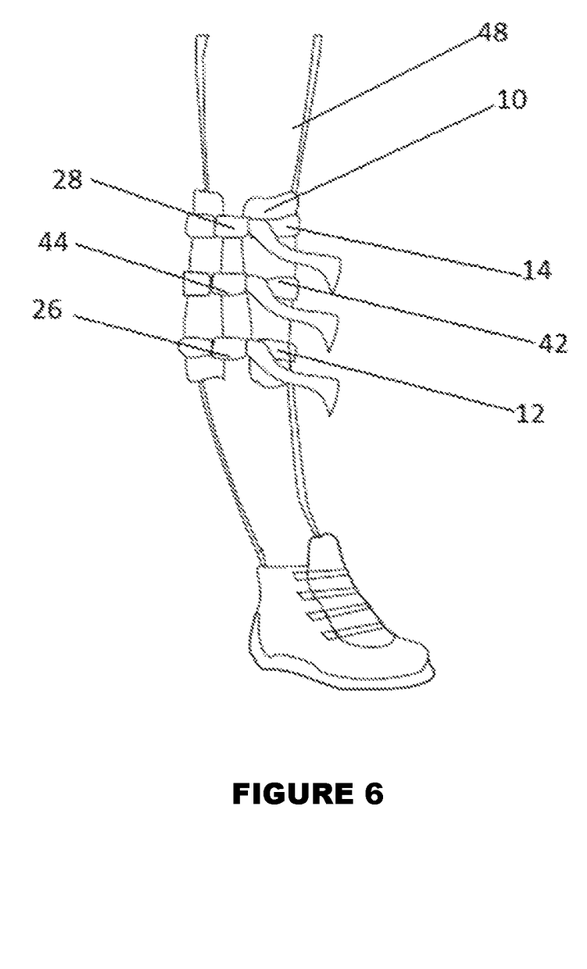
FIG. 6 is a perspective view from the other side of the multipurpose first aid apparatus of FIG. 5.

Referring to FIGS. 5 and 6 in particular, apparatus 1 is being used to splint or support the rider's leg 46 that has been injured. The injury may be a cut and the support is then used to help minimise the bleeding. The injury may be a sprain or fracture to a bond or joint. As illustrated the rider has sprained their knee while dismounting and so has used apparatus 1 to support the joint to make it possible to get back on the horse to ride home. To use apparatus 1 as a support or splint, anchors 16 and 18 have been unclipped, as have clips 26 and 28 so that straps 12 and 14 are free and body 10 can be unrolled to a rectangle of material. Zip 30 is unzipped to retrieve extra strap 42 and to remove pockets 34 and 36. If water is going to be used water is now filled into pocket 34 or 36. Optionally, a large removable plastic pocket may be included, and in this case this pocket may be filled with water. Zip 30 is zipped up and body 10 used to wrap around the injured area, in the example the knee of leg 46. Body 10 wraps tightly around the knee of leg 46 followed by strap 12 and strap 14. Each strap is wound around tightly and then clipped together using clips 26 and 28. In this way a strong support is provided to stabilise the injured knee joint. To further hold body 10 around the knee, extra strap 42 is used between strap 12 and strap 14 and clipped tightly together by clip 44.

Although illustrated for use on the rider, apparatus 1 can be used in exactly the same way to provide support to an injured leg of the horse or in other forms of the invention for a dog or other animal. The manner of use and support given is the same. The rider can support the injured leg of the horse quickly and easily so they can both seek professional assistance.

Reflective strip 48 can be seen in FIG. 5 running along the top outer surface of body 10. In use, when rolled up and attached to saddle 20 reflective strip 48 runs along the back of apparatus 1. Reflective strip 48 assists traffic to see the horse and rider on roads at night; in the case of an emergency situation lights will reflect off the strip and help to locate an injured horse and rider.

Figure 7:
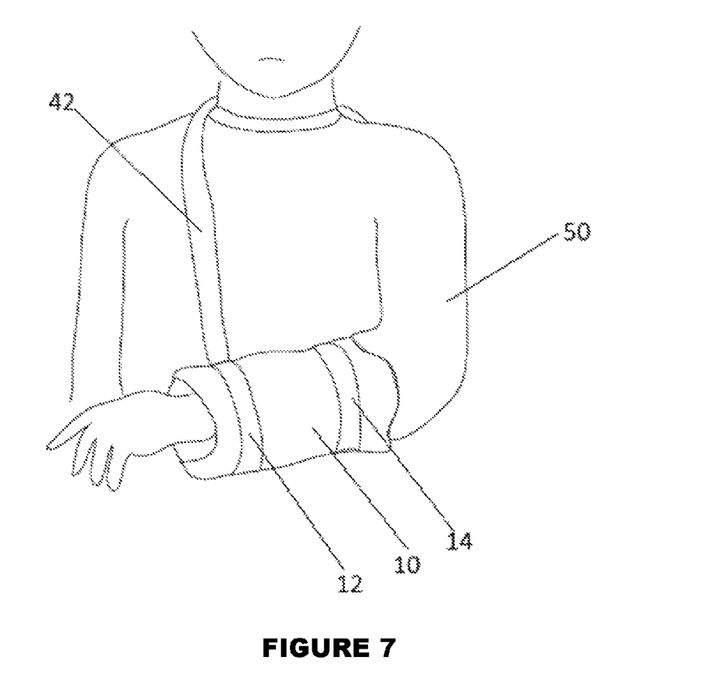
FIG. 7 is a front perspective view of the multipurpose first aid apparatus of FIGS. 1 to 6 in use to support the rider's injured arm.
Figure 8:
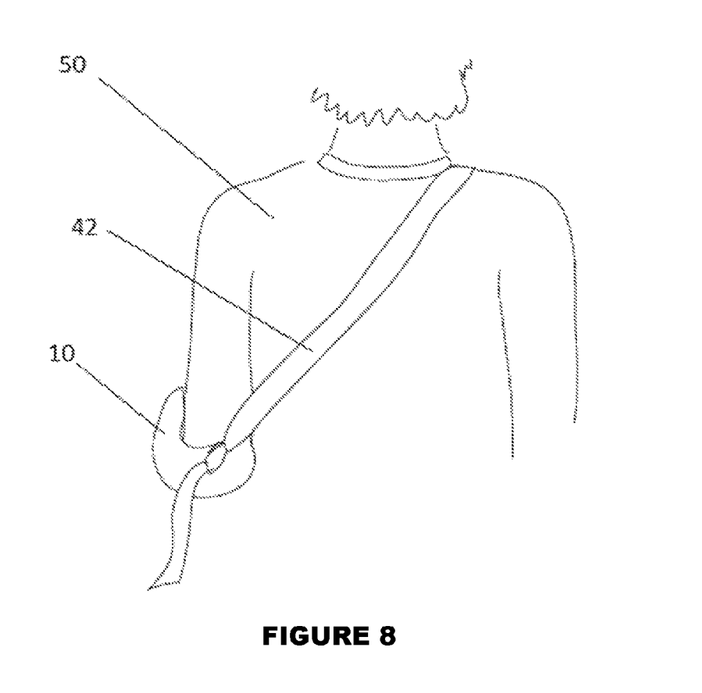
FIG. 8 is a back view of the multipurpose first aid apparatus of FIG. 7.

Referring to FIGS. 7 and 8 in particular apparatus 1 is shown used for an alternative injury of the rider to arm 50. Again body 10 is removed as described above and wrapped around the injured area of the rider's body. Again straps 12 and 14 are wrapped tightly and clipped to maintain body 10 tightly around the injured area. Extra strap 42 can be used in this case to create a sling for arm 50 by being attached to strap 12 round the neck of the person and across their back to attach to strap 14. The created sling supports the injured arm enabling the rider to ride or walk more comfortably until medical attention can be obtained. In another form of the invention extra strap 42 can be omitted and the two straps 12 and 14 themselves can be lengthened and connected together about the neck of the person to support an arm. In this form of the invention body 10 can be folded or rolled to form a tube or U-shaped support into which the arm of the person can be put and supported by the straps about the neck of the person.

Body 10 with use of straps 12, 14 and 42 can be used in other areas of the body of the rider or horse as required. Numerous different configurations of body 10 with straps 12 and 14 and if desired extra strap 42. In an emergency situation the easy to use straps and body 10 make apparatus quick and simple to use, without any specialist training, skills or knowledge. Survival books include the arrangement of splints and supports such as a sling but these are generally complex, tied from bandages or pieces of material. Use of apparatus 1 provides a strong support which can easy be assembled by any one without the need for more than very simple pictorial instructions.

Figure 9:
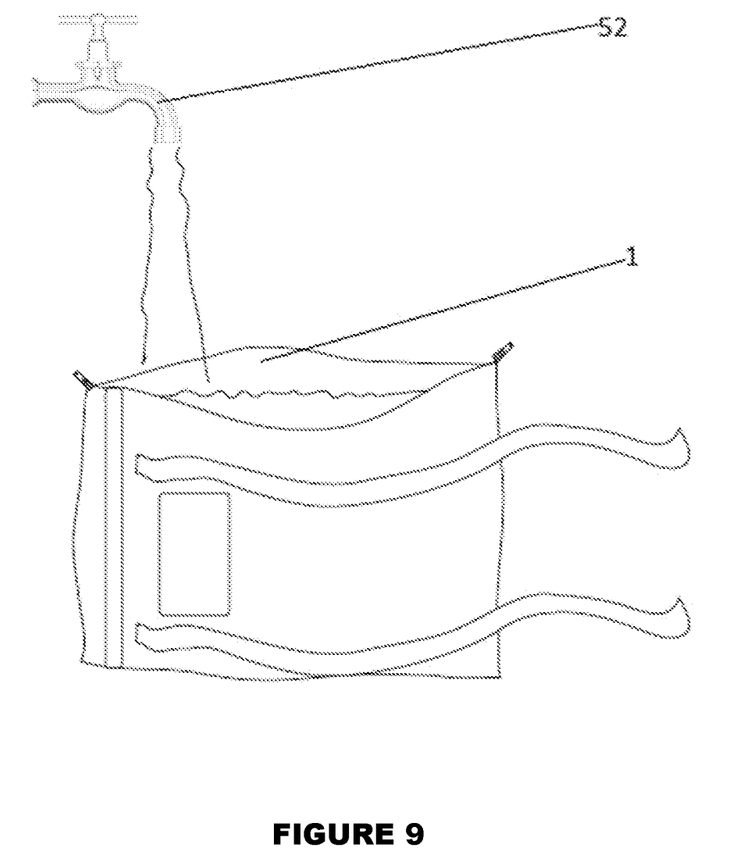
FIG. 9 is a perspective side view of the multipurpose first aid apparatus of FIGS. 1 to 8, being filled with water before use as a cooling support for an injured limb.

Referring to FIG. 9 it may be desired to fill body 1 with water from tap 52. Any available water source such as a creek, dam or stream could be used instead. Ice or even warm water could also be used if available and depending on the nature of the injury to be treated. For example, to reduce swelling and bruising it may be desirable to keep an injury cool. The water may be used not only for application of water to an injury but to carry water to drink or for other use in an emergency situation.

Overall apparatus 1 has numerous uses, on a day to day basis to carry useful items such as a mobile phone and first aid supplies but also in an emergency situation to be used to support an injured limb until professional help can be sought. The useful nature of apparatus 1 and the convenience and comfortable nature of its use is likely to mean rapid adoption in the equine community once seen, as it solves this long felt want for such a product. Where a person is in a remote situation, use of apparatus 1 is convenient by not interfering with travelling, allows ready access to mobile phone or other items and can support an injured limb of a person or animal in the case of an accident before seeking medical or veterinary assistance.

For any of the many and varied uses of the invention, the method of use is the same, no adaptation is needed, except for the inclusion of different items.

REFERENCE SIGNS LIST

| | |
|---|---|
| 1 | Apparatus |
| 10 | Body |
| 12 | Strap |
| 14 | Strap |
| 16 | Anchor |
| 18 | Anchor |
| 20 | Saddle |
| 22 | Loop |
| 24 | Loop |
| 26 | Clip 26a and 26b |
| 28 | Clip 28a and 28b |
| 30 | Zip |
| 32 | Pocket |
| 34 | Pocket |
| 36 | Pocket |
| 38 | Zip lock |
| 40 | Zip lock |
| 42 | Extra strap |
| 44 | Clip 44a and 44b |
| 46 | Rider's leg |
| 48 | Reflective strip |
| 50 | Arm |
| 52 | Tap |

The invention claimed is:

1. A multipurpose first aid apparatus for a person or animal comprising:
   a substantially rectangular and substantially waterproof body having a first surface, a second surface and an outer perimeter;
   fastening means disposed along the outer perimeter of the body, such that when the body is folded in half, the fastening means creates a pouch where the first surface becomes the interior of the pouch and the second surface becomes the exterior of the pouch;
   a plurality of compressing straps secured to the second surface of the body;
   a plurality of fasteners, each fastener attached to one of the plurality of compressing straps and enabling each compressing strap to be tightened or loosened to achieve a desired level of compression;
   an exterior pocket attached to the second surface of the body in a location where the exterior pocket is accessible when the body is folded into a pouch and rolled; and
   a plurality of sealable interior pouches removably attached to the first surface of the body, the interior pouches being sized and shaped to contain first aid items, and having at least one transparent surface to enable visual inspection of the first aid items held within the pouch;
   wherein, in the case of an injury to a limb of the person or animal, the body is formed into a pouch and wrapped around the limb that requires support and wherein once the body is wrapped around the limb, the plurality of compressing straps are secured around the body via the fasteners and tightened to a desired level of compression to firmly support the limb of the person or animal until professional medical or veterinary assistance can be sought.

2. The multipurpose first aid apparatus of claim 1 wherein the fastening means is a zipper.

3. The multipurpose first aid apparatus of claim 1 wherein the fastening means is substantially waterproof.

4. The multipurpose first aid apparatus of claim 1 wherein at least one of the plurality of interior pouches is waterproof and wherein the at least one waterproof interior pouch is filled with water to aid compression when the body is wrapped around the limb of the person or animal.

5. The multipurpose first aid apparatus of claim 1 wherein at least one of the plurality of compression straps includes an attachment means.

6. The multipurpose first aid apparatus of claim 5 wherein the attachment means is a strap.

7. The multipurpose first aid apparatus of claim 1 further comprising one or more attachment means secured to the second surface of the body.

8. The multipurpose first aid apparatus of claim 7 wherein the attachment means is a strap.

9. The multipurpose first aid apparatus of claim 1 further comprising a reflective strip attached to the second surface of the body.

10. The multipurpose first aid apparatus of claim 1 further comprising a support strap, wherein the support strap is wrapped around the injured person or animal and secured to the body or to one or more of the plurality of compressing straps to create a sling.

11. The multipurpose first aid apparatus of claim 1 wherein the exterior pocket is sized and shaped to carrying small electronic items.

12. A method of supporting an injured limb of a person or animal comprising:
   a. providing a multipurpose first aid apparatus for a person or animal comprising:
      i. a substantially rectangular and substantially waterproof body having a first surface, a second surface and an outer perimeter;
      ii. fastening means disposed along the outer perimeter of the body, such that when the body is folded in half, the fastening means creates a pouch where the first surface becomes the interior of the pouch and the second surface becomes the exterior of the pouch;
      iii. a plurality of compressing straps secured to the second surface of the body;
      iv. a plurality of fasteners, each fastener attached to one of the plurality of compressing straps and enabling each compressing strap to be tightened or loosened to achieve a desired level of compression;
      v. an exterior pocket attached to the second surface of the body in a location where the exterior pocket is accessible when the body is folded into a pouch and rolled; and
      vi. a plurality of sealable interior pouches removably attached to the first surface of the body, the interior pouches being sized and shaped to contain first aid items, and having at least one transparent surface to enable visual inspection of the first aid items held within the pouch;
      vii. wherein, in the case of an injury to a limb of the person or animal, the body is formed into a pouch and wrapped around the limb that requires support and wherein once the body is wrapped around the limb, the plurality of compressing straps are secured around the body using the securing clips and tightened to a desired tightness to firmly support the limb of the person or animal until professional medical or veterinary assistance can be sought;
   b. folding the body to form a pouch and securing the pouch via the fastening means;

c. wrapping the body around an injured limb of a person or animal;
d. securing the compressing straps via the fasteners and tightening the compressing straps to the desired level of compression.

13. The method of claim 12 wherein at least one of the interior pouches is waterproof and further comprising the step of filling the waterproof interior pouch with water and removably attaching the waterproof interior pouch to the first surface of the body before folding the body to form a pouch.

* * * * *